United States Patent [19]

Tamborski et al.

[11] 4,267,348

[45] May 12, 1981

[54] FLUORINE-CONTAINING BENZIMIDAZOLES

[75] Inventors: Christ Tamborski, Dayton; John B. Christian, Yellow Springs, both of Ohio

[73] Assignee: The United States of America as represented by the Secretary of the Air Force, Washington, D.C.

[21] Appl. No.: 100,301

[22] Filed: Dec. 4, 1979

[51] Int. Cl.³ .......................................... C07D 235/04
[52] U.S. Cl. ...................................................... 548/330
[58] Field of Search ........................................ 548/330

[56] References Cited

U.S. PATENT DOCUMENTS

| | | | |
|---|---|---|---|
| 3,849,431 | 11/1974 | Gallay et al. | 548/330 |
| 4,085,137 | 4/1978 | Mitsch et al. | 548/300 |
| 4,132,660 | 1/1979 | Christian et al. | 252/51.5 |

OTHER PUBLICATIONS

Mamedov et al., Igv. Akad. Nauk USSR, Ser. Khim, 1964, pp. 698–704.
Chem. Abs. 64: 2685g.

*Primary Examiner*—Ethel G. Love
*Attorney, Agent, or Firm*—Donald J. Singer; William J. O'Brien

[57] ABSTRACT

Benzimidazoles substituted in the 2-position with a perfluoroalkyleneether radical. The compounds are useful as antirust and anticorrosion additives in grease formulations based on fluorine-containing fluids.

5 Claims, No Drawings

FLUORINE-CONTAINING BENZIMIDAZOLES

RIGHTS OF THE GOVERNMENT

The invention described herein may be manufactured and used by or for the Government of the United States for all governmental purposes without the payment of any royalty.

FIELD OF THE INVENTION

This invention relates to benzimidazoles which are substituted in the 2-position with perfluoroalkyleneether groups.

BACKGROUND OF THE INVENTION

Benzimidazoles substituted in the 2-position with hydrocarbon alkyl and hydrocarbon aryl groups are well known compounds. For example, in Elderfield's "Heterocyclic Compounds", John Wiley and Sons, Inc., New York, New York, such 2-substituted benzimidazoles and processes for their preparation are disclosed. Also, the literature describes benzimidazoles that are substituted with perfluoroalkyl groups. While various 2-substituted benzimidazoles are disclosed by Elderfield as well as in other publications, e.g., "Imidazole and Its Derivatives" by Klaus Hofmann, Interscience Publishers, New York, New York, the prior art makes no mention of benzimidazoles substituted in the 2-position with a perfluoroalkyleneether group.

It is a principal object of this invention, therefore, to provide benzimidazoles substituted with perfluoroalkyleneether radicals.

Another object of the invention is to provide a process for preparing the 2-substituted benzimidazoles.

Other objects and advantages of the invention will become apparent to those skilled in the art upon consideration of the ensuing disclosure.

SUMMARY OF THE INVENTION

The present invention resides in benzimidazoles having the following structural formula:

$$\text{(I)} \quad \text{benzimidazole–C–R}_f$$

wherein $R_f$ is a perfluoroalkyleneether radical. Examples of perfluoroalkyleneether radicals include $CF_2(OCF_2CF_2)_xOC_2F_5$, where x is zero or an integer from 1 to 10, inclusive, and $CF(CF_3)[OCF_2CF(CF_3)]_yOC_3F_7$, where y is zero or an integer from 1 to 10, inclusive.

The benzimidazoles of this invention are synthesized by reacting o-phenylenediamine with a perfluoroalkyleneether imidate ester. The reaction involved in preparing the compounds can be represented by the following equation:

$$\text{(II)} + R_fC(=NH)\text{—OCH}_3 \xrightarrow[\text{HFIP}]{\text{HAC}} \text{(I)}$$

In the foregoing equation, $R_f$ is a perfluoroalkyleneether as described above. As shown by the equation, the reaction between o-phenylenediamine (II) and imidate ester (III) is conducted in the presence of glacial acetic acid (HAC), utilizing hexafluoroisopropanol (HFIP) as the reaction medium. The reaction temperature usually ranges from about 45° to 50° C. The reaction period is generally from about 1 to 4 days although shorter and longer periods may be employed.

The imidate esters utilized in the process are well known compounds that are disclosed in the literature. For example, H. C. Brown and C. R. Wetzel in Journal of Organic Chemistry, 30, 3724 (1965) describe a procedure for synthesizing a variety of imidate esters from a variety of fluorine-containing nitriles.

Another process for preparing the benzimidazoles can be represented by the following equations:

$$\text{(II)} + RLi \longrightarrow \text{(V)} \quad (2)$$

$$\text{(V)} + R_fCOR' \longrightarrow \text{(VII)} \quad (3)$$

$$\text{(VII)} \xrightarrow{P_2O_5} \text{(I)} \quad (4)$$

In the foregoing equations, R is an alkyl radical, such as $C_4H_9$, R' is also an alkyl radical, such as $CH_3$ or $C_2H_5$, and $R_f$ is a perfluoroalkyleneether group as described above.

As shown by equation 2, o-phenylenediamine (II) is reacted with an organolithium (IV), such as n-butyllithium, to give lithium salt (V). The reaction between the lithium salt (V) and the ester (VI) (equation 3) leads to the mono acylated product (VII). Isolation of this amide (VII) and dehydration with polyphosphoric acid (equation 4) provides the benzimidazole (I) in excellent yields.

A more complete understanding of the invention can be obtained by referring to the following illustrative examples which are not intended, however, to be unduly limitative of the invention.

EXAMPLE I

Synthesis of

-continued

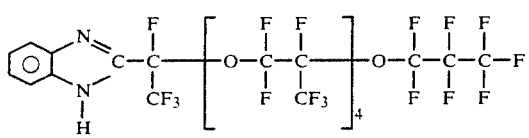

o-Phenylenediamine (0.761 g; 0.00705 moles) was dissolved in a mixture of hexafluoroisopropanol (20 ml) and glacial acetic acid (1.0 ml) and placed in a three-necked flask equipped with a water condensor, thermometer and addition funnel. While stirring the contents under nitrogen at room temperature, the hexamerimidate methyl ester C₃F₇O[CF(CF₃)CF₂O]₄CF(CF₃)C(=NH)OCH₃ (7.1 g; 0.00705 moles), was added from the addition funnel. No noticeable increase in temperature was noted. The contents were heated between 50°-55° C. and maintained at this temperature for a total of 90 hours. Periodic gas chromatography analysis indicated the complete consumption of the imidate ester. The reaction mixture was cooled, diluted with water whereupon a heavy liquid separated. The liquid was phase separated, washed repeatedly with water, taken up in diethyl ether, and dried over molecular sieves. After removing the solvent on a rotary evaporator, the crude benzimidazole (6.7 g; 89% yield) was obtained. Recrystallization from CH₂Cl₂ yielded a white waxy solid, m.p. 79°-81° C. Mass spectral analysis showed a M+ 1066 (expected M+ 1066). Its infrared spectrum (KBr) was characteristic of a fluorinated benzimidazole showing a broad N-H absorption between 2700 and 3300 cm⁻¹. A dilute solution in 1,1,3-trifluorotrichloroethane solvent gave a sharp absorption at 3490 cm⁻¹ due to free N-H. NMR analysis was consistent with the structure.

Analysis Calc'd: C,27.02; H,0.47; N,2.63% Found: C,27.16; H,0.30; N,2.65%.

EXAMPLE II

Synthesis of

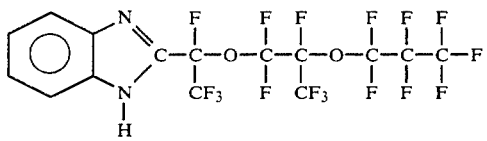

(a) Preparation of

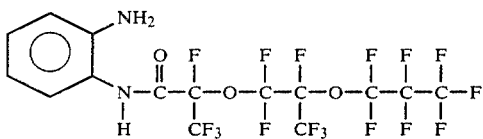

o-Phenylenediamine (7.56 g; 0.07 mole) was dissolved in anhydrous diethylether (400 ml) and placed in a four-necked flask fitted with a water condensor, two addition funnels and a thermometer. While stirring the contents under an atmosphere of nitrogen, the flask was cooled to about 0° C. n-Butyllithium (4.48 g; 0.07 moles, in 30.7 ml of a 2.28 M solution in hexane) was added during twenty minutes keeping the temperature below 5° C. The reaction mixture turned blue with the addition of n-butyllithium. To this mixture the ester C₃F₇OCF(CF₃)CF₂OCF(CF₃)C(O)OC₂H₅ (36.68 g; 0.07 moles) in anhydrous diethyl ether (10 ml) was added dropwise while keeping the temperature below 5° C. Addition took about 20 minutes, during which the color of the reaction mixture turned purple and finally deep brown. The contents were allowed to warm up to about 20° C. with continued stirring. Gas chromatography analysis of aliquot samples periodically removed indicated at slow reaction. After five days the reaction mixture was hydrolyzed with water. The diethylether layer was phase separated, dried and evaporated, yielding the crude monoamide product as a brown solid (39.7 g; 96.8% yield). Recrystallization from hexane gave a white product, m.p. 78°-79° C. Mass spectral analysis showed a M+ 586 (expected M+ 586). Its infrared spectrum (KBr) showed absorption at 3460 and 3380 cm⁻¹ due to a primary N-H bond, at 3320 cm⁻¹ due to a secondary amino group and a carbonyl bond at 1700 cm⁻¹, confirming the monoamide structure. NMR analysis was consistent with the structure.

Analysis Calc'd: C,30.7; H,1.19; N,4.78%, Found: C,30.82; H,0.98; N,4.80%.

(b) Cyclization of Amide to the Benzimidazole

The monoamide (12.5 g; 0.021 moles) was placed in a flask under dry nitrogen. Polyphosphoric acid (150 g) was added while vigorously stirring the mixture. The flask was heated between 140°-145° C. and maintained at this temperature for two hours. Considerable effervescence was observed. Gas chromatography analysis showed that the amide had completely reacted. The reaction mixture was cooled to about 100° C. and added slowly to crushed ice. The crude benzimidazole product separated, was washed with water and finally with sodium bicarbonate solution. The crude product, (11.3 g; 93% yield) was recrystallized from hexane to yield 8.95 g (74% yield) of pure benzimidazole, m.p. 115°-116° C. Mass spectral analysys showed a M+ 568 (expected M+ 568). Its infrared and NMR analysis were consistent with the benzimidazole structure.

Analysis Calc'd: C,31.69; H,0.88; N,4.93%, Found: C,31.85; H,0.86; N,4.87%.

As seen from the foregoing, the present invention provides benzimidazoles substituted with perfluoroalkyleneether groups. The benzimidazoles are particularly useful as antirust and anticorrosion additives for grease compositions. Use of the compounds as such additives is disclosed in our copending U.S. applications Ser. Nos. 100,180 and 100,179, both filed on December 4, 1979. The disclosures of these two applications are incorporated herein by reference.

As will be evident to those skilled in the art, modifications of the present invention can be made in view of the foregoing disclosure without departing from the spirit and scope of the invention.

We claim:

1. A fluorine-containing benzimidazole having the following structural formula:

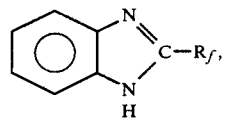

wherein R_f is an acyclic perfluoroalkyleneether radical.

2. The fluorine-containing benzimidazole of claim 1 in which R_f is CF₂(OCF₂CF₂)ₓOC₂F₅, where x is zero or an integer from 1 to 10, inclusive.

3. The fluorine-containing benzimidazole of claim 1 in which R_f is CF(CF₃)[OCF₂CF(CF₃)]ᵧOC₃F₇, where y is zero or an integer from 1 to 10, inclusive.

4. The fluorine-containing benzimidazole of claim 3 in which R_f is CF(CF₃)[OCF₂CF(CF₃)]₄OC₃F₇.

5. The fluorine-containing benzimidazole of claim 3 in which R_f is CF(CF₃)OCF₂CF(CF₃)OC₃F₇.

* * * * *